United States Patent [19]
Treml et al.

[11] Patent Number: 5,593,824
[45] Date of Patent: Jan. 14, 1997

[54] BIOLOGICAL REAGENT SPHERES

[75] Inventors: Suzanne B. Treml, Whitefish Bay; Cristine J. Dall, Shorewood; Connie A. Draveling, New Berlin; James F. Jolly, Glendale; Rama P. Ramanujam, Brookfield, all of Wis.

[73] Assignee: Pharmacia Biotech, Inc., Milwaukee, Wis.

[21] Appl. No.: 420,933

[22] Filed: Apr. 12, 1995

Related U.S. Application Data

[63] Continuation-in-part of Ser. No. 300,015, Sep. 2, 1994.
[51] Int. Cl.$^6$ .................. C12Q 1/00; C12Q 1/34; C12Q 1/37; C12P 21/06
[52] U.S. Cl. .................. 435/4; 435/18; 435/23; 435/188; 435/68.1; 536/1.11; 536/25.4; 536/25.41; 536/124; 424/484; 424/488; 424/489
[58] Field of Search .................. 435/4, 18, 23, 435/188, 68.1; 536/1.11, 25.4, 25.41, 124; 424/484, 488, 489

[56] References Cited

U.S. PATENT DOCUMENTS

| | | | |
|---|---|---|---|
| 3,300,474 | 1/1967 | Flodin et al. | 260/209 |
| 3,456,050 | 7/1969 | Rieckmann et al. | 424/35 |
| 3,721,725 | 3/1973 | Briggs et al. | 264/6 |
| 3,932,943 | 1/1976 | Briggs et al. | 264/6 |
| 4,134,943 | 1/1979 | Knitsch | 264/28 |
| 4,372,942 | 2/1983 | Cimiluca | 424/16 |
| 4,423,086 | 12/1983 | Devos et al. | 427/3 |
| 4,559,298 | 12/1985 | Fahy | 435/1.1 |
| 4,655,047 | 4/1987 | Temple et al. | 62/64 |
| 4,712,310 | 12/1987 | Roy | 34/5 |
| 4,753,790 | 6/1988 | Silva et al. | 435/4 |
| 4,762,857 | 8/1988 | Bollin, Jr. et al. | 514/777 |
| 4,780,285 | 10/1988 | Kuypers et al. | 422/102 |
| 4,806,343 | 2/1989 | Carpenter et al. | 424/450 |
| 4,820,627 | 4/1989 | McGeehan | 435/4 |
| 4,848,094 | 7/1989 | Davis et al. | 62/64 |
| 4,863,856 | 9/1989 | Dean, Jr. et al. | 435/68.1 |
| 4,891,319 | 1/1990 | Roser | 435/188 |
| 4,897,353 | 1/1990 | Carpenter et al. | 435/188 |
| 4,898,781 | 2/1990 | Onouchi et al. | 435/188 |
| 4,997,654 | 3/1991 | Corsello et al. | 424/440 |
| 5,098,893 | 3/1992 | Franks et al. | 514/54 |
| 5,200,399 | 4/1993 | Wettlaufer et al. | 514/23 |
| 5,240,843 | 8/1993 | Gibson et al. | 435/188 |
| 5,250,429 | 10/1993 | Jolly et al. | 435/18 |
| 5,288,502 | 2/1994 | McGinity et al. | 424/484 |

FOREIGN PATENT DOCUMENTS

| | | |
|---|---|---|
| 0252750 | 1/1988 | European Pat. Off. . |
| 0383569 | 8/1990 | European Pat. Off. . |
| 60129102 | 7/1985 | Japan . |
| WO86/00336 | 1/1986 | WIPO . |
| WO93/04195 | 3/1988 | WIPO . |

OTHER PUBLICATIONS

A. Kassem, et al., "Preparation of Non-pareil Seeds . . . ," *Pharm. Ind.* 40[4]:396–399, 1978.
M. Brophy, et al., "Influence of coating and core modifications . . . ," *J. Pharm. Pharmacol.* 33:495–499, 1981.
I. Ghebre-Sellassie, et al., ". . . High Speed Pelletization . . . ," 11 *Drug Devel. & Indus. Pharm.* 1523–1541, 1985.
G. Orndorff, et al., ". . . Preservation of *E. coli*," 10 *Cryobiology* 475–487, 1973.
A. MacKenzie, "Collapse during freeze drying . . . ," in *Freeze Drying and Advanced Food Techology*, S. Goldblith, et al. (Eds.), Academic Press, London, pp. 277–307, 1975.
J. Carpenter, et al., "Stabilization of Phosphofructokinase . . . " 24 *Cryobiology* 455–464, 1987.
F. Franks, ". . . Stabilization of Biologicals," 12 *Bio/Technology* 253–256, 1994.
R. Ramanujam, et al., "Ambient–Temperature–Stable Molecular Biology Reagents," 14(3) *Biotechniques* 470–474, 1993.

*Primary Examiner*—John Kight
*Assistant Examiner*—Louise Leary
*Attorney, Agent, or Firm*—Quarles & Brady

[57] ABSTRACT

A reagent sphere is disclosed comprising at least one biological reagent and a glass-forming filler material in a concentration sufficient to facilitate formation of a glassy, porous composition, wherein the reagent semi-sphere is water soluble and has a $T_g$ sufficient for room temperature stability. At least two carbohydrates are combined to create the reagent sphere. The first carbohydrate is a synthetic high molecular weight polymer. The second carbohydrate is different than the first carbohydrate. A method is provided for making the reagent sphere.

32 Claims, No Drawings

BIOLOGICAL REAGENT SPHERES

This application is a continuation-in-part of copending U.S. Ser. No 08/300,015, filed Sep. 2, 1994, which is incorporated by reference as if fully set forth below.

FIELD OF THE INVENTION

This invention relates to the long-term storage of biological materials and reagents. In particular, it relates to compositions for glassy, porous reagent spheres with a $T_g$ of 10° C. or more and methods for making the same.

BACKGROUND

Few biologically active materials are sufficiently stable so that they can be isolated, purified, and then stored in solution at room temperature. Typically, biological reagents are stored in a glycerol solution which is maintained at temperatures of 4° C., −20° C. or −70° C. They may be stored in bulk and then combined with other reagents before use.

Biological reagents are sometimes also provided in dried form to increase their storage stability. Furthermore, in preparing reagents for convenient and efficient testing of biological samples, it is frequently important to obtain dry chemical blends in uniform, discreet amounts. These reagents must be efficiently and economically prepared in small, precisely measured quantities. Current technology for producing dry biological reagent compositions involves procedures such as dry-blending, spray-drying, freeze-drying, fluidized bed drying, and/or cryogenic freezing. All these procedures, however, have limitations and drawbacks.

In dry-blending technology, it is often difficult to obtain homogeneous blends of chemicals due to their different densities. Furthermore, homogeneity is especially difficult to achieve when very small amounts of ingredients are mixed with large amounts of others. Even if homogeneity is achieved, it is most difficult to reproducibly dispense small amounts of the blended biological chemicals.

Spray-drying technology provides more homogeneous blends of chemicals because the reagents are first dissolved in solution. See U.S. Pat. No. 4,712,310. For an example of the use of spray-drying along with fluidized bed technology see A. Kassem, et al., 40 *Pharm. Ind.* 396–399 (1978) and M. Brophy, et al., 33 *J. Pharm. Pharmacol.* 495–499 (1981). With spray-drying, however, it is difficult to dispense precise amounts of blended chemicals. To overcome this drawback, the resulting particles are usually reprocessed by agglomeration to obtain uniform particle sizes such as tablets. However, the agglomerated particles are generally less soluble than the original spray-dried particles or powders. Also, these procedures sometimes use fluorocarbon cryogenic solutions which can be hazardous to the environment. The disclosure of the above articles and patents, and of all other articles and patents recited herein, are incorporated by reference as if fully set forth herein.

Fluid bed technology relies upon spraying a liquid reagent blend onto a particle and drying the composition to obtain a particle coated with blended reagents. For examples of this technology, see, for example, U.S. Pat. No. 4,820,627 and I. Ghebre-Sellassie, et al., 11 *Drug Devel. and Indus. Pharm.* 1523–1541 (1985). However, using fluid bed technology, it is difficult to obtain uniformly sized particles and to produce a uniform coating.

Another method for stabilizing biologicals is freeze-drying. For examples of various applications of freeze-drying technology see, for example, G. Orndorff, et al., 10 *Cryobiology* 475–487 (1973); A. MacKenzie, in *Freeze-drying and Advanced Food Technology*, S. Goldblith, et al. (Eds.), Academic Press, London (1975); U.S. Pat. No. 3,721,725; U.S. Pat. No. 4,134,943; U.S. Pat. No. 4,762,857; U.S. Pat. No. 4,806,343; U.S. Pat. No. 4,897,353; and Japanese patent Application No. 0129102. One drawback to the freeze-drying is the use of fluorocarbon refrigerants which may be dangerous to the environment.

Another method of stabilizing biologicals is by air-drying biological reagent compositions. For examples of air-drying of biological compositions using disaccharides as stabilizers see J. Carpenter, et al., 24 *Cryobiology* 455–464 (1987) and U.S. Pat. No. 4,891,319. Some problems with air drying processes are that the dried product is not in readily dispensable form. Also, the biological reagents must be stable at or above the temperature of the drying process.

One specialized process using freeze-drying technology is the formation of droplets or spheres which are contacted with a cryogenic liquid and then freeze-dried. For examples see U.S. Pat. No. 3,932,943; U.S. Pat. No. 4,780,285; U.S. Pat. No. 4,848,094; U.S. Pat. No. 4,863,856; and PCT Application WO93/04195. One drawback of this technology is that the reagent spheres are fragile and tend to disintegrate.

One type of carrier or filler which has been used to stabilize biological reagents are glass-forming filler materials. The biological reagent solutions are incorporated into the glass-forming filler materials (which are water soluble or a water-swellable substance). They are then dried to produce a glassy composition which immobilizes and stabilizes the biological reagent. For examples of glass-forming filler materials for stabilizing biological reagents see, for example, F. Franks, 12 *Bio-Technology* 253 (1994); U.S. Pat. No. 5,098,893; U.S. Pat. No. 5,200,399; and U.S. Pat. No. 5,240,843.

Carbohydrates such as glucose, sucrose, maltose or maltotriose are an important group of glass-forming substances. Other polyhydroxy compounds can be used such as carbohydrate derivatives like sorbitol and chemically modified carbohydrates. Another important class of glass-forming substances are synthetic polymers such as polyvinyl pyrrolidone, polyacrylamide, or polyethyleneimine.

Further examples of glass-forming substances include sugar copolymers such as those sold by Pharmacia under the registered trademark FICOLL. FICOLL resin is disclosed in U.S. Pat. No. 3,300,474 which describes the materials as having molecular weights of 5,000 to 1,000,000 and as containing sucrose residues linked through ether bridges to bifunctional groups. Such groups may be an alkylene of 2, 3 or more carbon atoms but not normally more than 10 carbon atoms. The bifunctional groups serve to connect sugar residues together. These polymers may, for example, be made by reaction of sugar with a halohydrin or bis-epoxy compound. A glass is typically defined as an undercooled liquid with a very high viscosity, that is to say at least $10^{13}$ Pa×s, probably $10^{14}$ Pa's or more.

One drawback of the aforementioned references is that normally the stabilized and glassified biological materials are ground into powders, compounded into tablets, or maintained in a thin glassy film in a container like a microcentrifuge tube. This type of packaging is generally inconvenient because dosages of a powdered material are difficult to measure, compounded tablets are slow to dissolve, and excessive time is needed to dissolve a thin glassy film disposed in a microcentrifuge tube.

Numerous methods to make and use compositions of glassy immobilized biological materials have been tried.

One system mentioned above is utilizing a thin glassy film dried and disposed in a container suitable to the final user, such as a microcentrifuge tube. However, attempts have been made to reduce the associated packaging cost by converting the glassy format to a tablet, pellet, or sphere which could be packaged in bulk containers ready for individual use. Various techniques have been tried such as a tablet press, centrifugal granulator, and fluid bed coating and vacuum drying droplets on a flat surface. Each process resulted in limited success.

The tablet press makes easily handled pills but the pills dissolve slowly. The use of tabletting excipients designed to increase dissolution speed interfere with enzyme activity. The centrifugal granulator makes spheres but the size distribution was too large to make individual dispensing practical and all enzyme activity was lost during the drying step. Fluid bed coating made spheres with good size distribution, and activity, but poor solubility. Vacuum drying droplets with a standard low viscosity solution, such as 8%–20% solids, produced flat fragile disks which dissolved slowly.

Glassy substances are also used as hard coatings for candies and pharmaceuticals. Examples of these are found in U.S. Pat. No. 3,456,050; U.S. Pat. No. 4,372,942; U.S. Pat. No. 4,423,086; U.S. Pat. No. 4,559,298; U.S. Pat. No. 4,753,790; U.S. Pat. No. 4,898,781; U.S. Pat. No. 4,997,654; PCT Publication No. W086/00336; and European Patent Application No. 0 252 750.

Accordingly, there is a need for a glassy format biological reagent which possesses excellent water solubility and dissolution rate, possesses a porous structure to assist with dissolution, avoids the typically fragile nature of the reagent Spheres disclosed in PCT Publication No. W093/04195 (supra), can be made by a method which allows manipulation of droplet size characteristics, and which can be dispensed from a holder such as that disclosed in U.S. Pat. No. 4,780,285.

SUMMARY OF THE INVENTION

We have discovered a homogeneous solution of glass-forming filler material, biological reagent, and water which provides a viscosity such that controlled droplets can be dispensed on an inert cryogenic surface and vacuum dried so as to form a spherical biological reagent that is stable at room temperature and soluble in water.

In a first aspect of the invention, the invention provides a biological reagent sphere comprising at least one biological reagent and a glass-forming filler material in a concentration sufficient to facilitate formation of a glassy, porous composition. The glass-forming filler comprises a mixture of a high molecular weight synthetic polymer and a second carbohydrate. The carbohydrate polymer is preferably a synthetic polymer made by the copolymerization of sucrose and epichlorohydrin and has a molecular weight of at least 50,000. The second carbohydrate is preferably melezitose.

The reagent sphere is water soluble and has a $T_g$ sufficient for room temperature stability. Preferably, the reagent sphere has structural integrity.

The biological reagent sphere is capable of completely dissolving in 20 µl of aqueous solution in less than 1 minute, preferably 30 seconds. The reagent sphere preferably has a moisture content of less than 10%. The reagent sphere may have a diameter of about 2 mm to about 6 mm. Preferably, the reagent sphere has a diameter of about 2.5 mm.

The reagent sphere may have at least one reagent which is unstable when alone in an aqueous solution at room temperature. The reagent sphere may also comprise a plurality of reagents which may or may not react with each other when in aqueous solution at room temperature.

The biological reagent used in the sphere is preferably selected from at least one of the group consisting of DNA/RNA modifying enzymes, restriction enzymes, nucleotides, oligonucleotides, proteins, enzymes, DNA, and nucleic acids.

In one embodiment of the present invention, the glass-forming filler material comprises a high molecular weight carbohydrate polymer, such as FICOLL resin, and at least one of the group of carbohydrates consisting of melezitose, cellobiose, DEXTRANT10 resin, maitotriose, maltose, cyclodextran, sorbitol, trehalose, PEG, and sucrose. Preferably, melezitose, cellobiose, dextranT10, or maltotriose are chosen. Most preferably, melezitose is chosen.

In another version of the invention a reagent kit is provided comprising at least one reagent sphere according to the first version of the invention, a receptacle containing the reagent sphere, a sealed foil pouch containing the tube and a desiccant, and, optionally, a dispenser device adapted for individually dispensing at least one reagent sphere. Preferably, the receptacle is a microfuge tube or a microtiter plate.

A further version of the invention provides a method of making a reagent sphere comprising the steps of: providing an aqueous solution of a buffered biological reagent; providing glass-forming filler materials comprising a mixture of a high molecular weight carbohydrate polymer and a second carbohydrate; mixing the glass-forming filler materials with the buffered biological reagent solution to form a homogeneous solution wherein the concentration of the filler material is sufficient to facilitate formation of a glassy, porous composition having a predetermined spherical shape; dispensing the mixture in the form of substantially uniform droplets; collecting the droplets on an inert cryogenic medium to form spheres; and drying the droplets under conditions suitable for maintaining the predetermined spherical shape, to form the reagent sphere; wherein the reagent sphere is water soluble and has a $T_g$ sufficient for room temperature stability. The mixture is preferably a homogeneous solution.

Preferably, the homogeneous solution contains 10% to 50% solids.

In another embodiment, the present invention provides a reagent sphere made according to the above method.

It is therefore an objective and advantage of the present invention to provide a biological reagent sphere and methods of making the same.

Other objects and advantages of the present invention are:

(a) providing a homogeneous solution of biological reagent(s), glass forming filler material, and water wherein the shape of droplets formed on an inert cryogenic surface can be controlled by changing the percent solids of the emulsion;

(b) wherein the shape of the droplet can be varied by changing the surface composition or shape of the drying surface;

(c) wherein the shape of the droplets can be controlled by manipulating the vacuum level during drying;

(d) wherein the drying rate can be used to preserve the shape and activity of the reagent sphere;

(e) providing a reagent sphere which is resistant to degradation and mechanical shock;

(f) providing a reagent sphere having a porous structure which assists in the dissolution rate of the reagent sphere;

(g) providing reagent spheres which can be dispensed individually from an appropriately adapted dispenser device; and (h) providing stable storage of a biological reagent that would otherwise be unstable when alone in an aqueous solution at room temperature and providing stable storage of a plurality of biological reagents that would otherwise react with each other when in an aqueous solution at room temperature.

These and still other objects and advantages of the invention will be apparent from the description below. However, this description is only of the preferred embodiments. The claims, therefore, should be looked to in order to assess the whole scope of the invention.

DETAILED DESCRIPTION OF THE INVENTION

Selection of Glass-Forming Filler Material

The formulation of the reagent sphere contains glass-forming filler material comprising a mixture of a high molecular weight synthetic carbohydrate polymer and a second carbohydrate. We have found that one needs two different carbohydrates to produce a reagent sphere with the desired characteristics (described below). The synthetic carbohydrate polymer provides structural integrity, and the second carbohydrate provides increased solubility. The formulation of the present invention may contain more than two different carbohydrates, but will always contain a high molecular weight synthetic carbohydrate polymer and at least one second carbohydrate.

Preferably, the second carbohydrate is at least one of the following carbohydrates: melezitose, cellobiose, DEXTRANT10 resin, maltotriose, maltose, cyclodextran, sorbitol, trehalose, PEG, and sucrose. Most preferably, the carbohydrate is selected from melezitose, cellobiose, DEXTRANT10 resin and maltotriose. Most preferably, the carbohydrate is melezitose.

The high molecular weight synthetic polymer has a molecular weight of at least 10,000, preferably 50,000. Most preferably, the polymer has a molecular weight of at least 70,000. By "synthetic" we mean that the polymer is artificially created and not found in nature. The polymer is preferably made by the copolymerization of sucrose and epichlorohydrin. One commercially available product is FICOLL synthetic polymer. The general chemical structure of FICOLL resin is $(-O-R-O-CH_2-CH(OH)-CH_z-)n$. For FICOLL400 resin, n=398. For FICOLL70 resin, =n=68. FICOLL400 resin and FICOLL70 resin (both available from Pharmacia Biotech Inc., Milwaukee, Wis.) are both preferred versions of FICOLL resin. Preferably, a 50/50 mix of FICOLL70 resin and FICOLL400 resin is used.

The high molecular weight polymer concentration can be between 5% to 25% (weight\volume) of the reagent preparation but is preferably 12.5% to 15%. The second carbohydrate is 5% to 15% (w/v).

The percent solids in the reagent sphere is between 10% to 50%. Preferably, the percent solids are between 20% and 30%. The percent solids in the formulations described in the examples ranged from 21% for PCR reactions to 29% for DNA labelling reactions. The carbohydrates provide most of the mass in the formulations. Typically the buffer and enzymes account for 0.25–0.4 mg in any formulation. The carbohydrate polymer accounted for 1.25–1.75 mg and melezitose accounts for 0.5–1 mg in any formulation described in the example.

As described above, the glass-forming materials must be chosen so that the resulting sphere has structural integrity. By "structural integrity" we mean that the sphere can withstand handling and packaging and maintain its shape. Typically, less than 10% of the sphere is lost in handling. Preferably, less than 5% of the sphere material is lost due to handling. Typical handling might include storage of the sphere together with other spheres and removal of the sphere for individual application into a chemical mixture.

Selection of a Biological Reagent

Many biological reagents are suitable for storage by the method of the present invention. Also, the biological reagent compositions of the present invention are particularly suitable for performing a wide variety of analytical procedures which are beneficially or necessarily performed on blood plasma or diluted plasma.

The analytical procedures will generally require that the blood plasma be combined with one or more reagent spheres so that some optically detectable change occurs in the plasma which may be related to measurement of a particular component or characteristic of the plasma. Preferably, the plasma will undergo a reaction or other change which results in a changing color, fluorescence, luminescence or the like, which may be measured by conventional spectrophotometers, fluorometers, light detectors, etc. In some cases, immunoassays and other specific binding assays may be performed.

A still further category of biological reagents to which the present invention is applicable is protein and peptides, including derivatives thereof such as glycoproteins. Such proteins and peptides may be any of: enzymes, transport proteins (for example hemoglobin, immunoglobulins, hormones, blood clotting factors and pharmacologically active proteins or peptides).

Another category of biological reagents to which the invention is applicable comprises nucleosides, nucleotides (such as deoxynucleotides, ribonucleotides and dideoxynucleotides), dinucleotides, oligonucleotides and also enzyme cofactors, whether or not these are nucleotides. Enzyme substrates in general are also biological reagents to which the invention may be applied.

Another embodiment of this invention is to provide nucleic acid extraction and purification reagents in convenient formats. Particularly, chaotropic reagents and nucleic acid extraction and binding reagents are desired.

An example of a nucleic acid extraction reagent is SDS and other detergents.

A chaotropic reagent or salt is one that dissolves a biological sample by interrupting weak intermolecular forces like van der Waal's attractions. Van der Waal's attractions hold lipid bilayer membranes together. Chaotropic salts solubilize proteins, dissolve cells, denature nucleic acids, and allow nucleic acids to bind to solid support. Chaotropic salts include GITC, isothcyanate, sodium perchlorate, iodides, trifluroacetates, urea, trichloroacetates, alkali metal perchlorate and thiocyanates.

Nucleic acid binding reagents as solid support include ion exchangers [carboxymethylated cellulose (CM), diethylaminomethyl cellulose (DEAE), triethylaminomethyl cellulose (TEAE), divinylbenzene (DVB)], silica particles, latex particles, controlled pore glass (CPG) nitrocellulose material, polystyrene, derivatized magnetic particles, and chemically modified functional groups on acrylamides and agarose.

The biological reagent for stabilization in storage may be isolated from a natural source, animal, plant, fungal or bacterial, or may be produced by and isolated from cells grown by fermentation and artificial culture. Such cells may or may not be genetically transformed cells.

Another development of this invention is to store more than one reagent of a reacting system in a glass reagent sphere. This can be useful for materials which will be required to be used together in, for example, an assay or a diagnostic kit.

Storing the reagents in a single glassy preparation provides them in a convenient form for eventual use. For instance, if an assay requires a combination of a substrate or cofactor and an enzyme, two or all three could be stored in a glassy reagent sphere in the required concentration ratio and be ready for use in the assay.

If multiple reagents are stored, they may be mixed together in an aqueous emulsion and then incorporated together into a glass. Alternatively, they may be incorporated individually into separate glasses which are then mixed together.

When multiple reagents are stored as a single composition (which may be two glasses mixed together) one or more of the reagents may be a protein, peptide, nucleoside, nucleotide, or enzyme cofactor. It is also possible that the reagents may be simpler species. For instance, a standard assay procedure may require pyruvate and NADH to be present together. Both can be stored alone with acceptable stability. However, when brought together in an aqueous solution they begin to react. If put together in required proportions in the glassy reagent sphere, they do not react and the glass can be stored. By react we mean any biochemical reaction.

The preferred biological reagents of the present invention are enzymes and cofactors that provide a reagent system to detect, amplify, modify or sequence nucleic acids. Such enzymes include but are not limited to DNA polymerases (e.g., Klenow), T7 DNA polymerase or various thermostable DNA polymerases such as Taq DNA polymerase; AMV or murine reverse transcriptase, T4 DNA ligase, T7, T3, SP6 RNA polymerase, and restriction enzymes. Cofactors include nucleotides, oligonucleotides, DNA, RNA, required salts for enzyme activity (e.g., magnesium, potassium and sodium), and salts required for buffer capacity. Buffer salts provide a proper pH range and aid stability. Some buffers which may be used include Tris pH 7.6–8.3.

Any potential biological reagents may be evaluated using a protocol according to Example 1, infra. Thus, suitable biological reagents are rendered stable in the reagent sphere as determined by a functionality test like that in Example 1.

Mixing

A typical formulation (using DNA labelling formulation as the example) is made as follows:

All reagents used are typically autoclaved or filter sterilized (preferably a 0.25 μm filter) before use. Formulations are made and stored on ice until spheres are dispensed. For 200 mls (enough for 20,000 spheres) of a DNA labelling formulation, 15 g each of Ficoll 400 and Ficoll 70 and 20 g melezitose are added to approximately 90 ml of sterile water and mixed on a stir plate until dissolved.

50 ml of a 20X concentrated DNA labelling buffer (200 mM Tris pH 7.5, 200 mM $MgCl_2$ 1M NaCl) is added along with 10 mls of a 10 mg/ml BSA solution. One ml each of 100 mM ATP, GTP, and TTP are added. Once all the reagents are in solution the formulation is stored on ice or under refrigeration until it is to be used for making spheres. Just before use, 400 Ku of Klenow fragment DNA polymerase is added (minimum concentration of stock should be 100 Ku/ml in order to keep the glycerol concentration below 1% in the sphere). Also just before use, 1200 $A_{260}$ Units of $d(N)_9$ primer is added. Before adding to the formulation, the primer should be heated at 65° C. for 7 minutes and quickly cooled on ice. After addition of the enzyme and primer, the final volume should be brought to 200 ml with sterile water. The density of the final solution will be 1.14 g/ml.

Dispensing

The final volume per dose of the reagent homogeneous solution is often small, such as 5–30 μl, preferably 10 μl, to allow a working volume of 10–100 μl when the sphere is dissolved in a working solution.

Spheres are typically formed by dispensing drops of homogeneous solution onto the surface of liquid nitrogen typically using an IVEK model AAA pump. The solution is dispensed as discrete drops in a volume ranging from 5 μl to 30 μl but preferably 10 μl. The sphere is formed as the solution falls through the air before reaching the surface of the liquid nitrogen. The distance between the dispensing needle and the liquid nitrogen surface is typically 1 to 6 inches. The rate of the pump depends on the volume being dispensed, the size of the needle and the viscosity of the solution. One drop is dispensed every 1 to 5 seconds. After the spheres are frozen they are dried by the protocols described later.

Dispensing the reagent homogeneous solution without causing high shear rates is difficult. However, using a valveless positive displacement pump such as those made by FMI or IVEC has been shown to work well. A time/pressure method such as that used to dispense adhesives also works well. However, using a pinch valve or peristaltic principle produced inconsistently sized drops.

Dispensing Medium

The homogeneous solution is dispensed onto a cryogenic liquid or onto a cryogenically cooled solid surface. By "cryogenic" we mean a liquified gas having a normal boiling point below about −75° C., preferably below about −150° C. The preferred cryogenic liquid is nitrogen. The frozen spheres are recovered and then freeze dried to a moisture content of less than about 10%, but preferably about 2%–6%.

Drying Process

The spheres formed by dispensing onto a cryogenic surface can be dried by using a freeze-drying process. Typical successful freeze-drying profiles are shown in Tables 1–4.

TABLE 1

| temperature (°C.) | vacuum (mTorr) | Time (min.) | comment |
| --- | --- | --- | --- |
| −50 | atm | 120 | hold |
| −46 | 40 | 240 | ramp |
| −46 | 40 | 900 | hold |
| −36 | 40 | 120 | ramp |
| −36 | 40 | 720 | hold |
| 28 | 40 | 180 | ramp |
| 28 | 40 | 300 | hold |

TABLE 2

| temperature (°C.) | vacuum (mTorr) | Time (min.) | comment |
|---|---|---|---|
| −50 | 40 | 30 | ramp |
| −50 | 40 | 1950 | hold |
| −48 | 40 | 30 | ramp |
| −48 | 40 | 240 | hold |
| −44 | 40 | 30 | ramp |
| −44 | 40 | 720 | hold |
| −36 | 40 | 30 | ramp |
| −36 | 40 | 480 | hold |
| 28 | 40 | 128 | ramp |
| 28 | 40 | 240 | hold |

TABLE 3

| Temperature (°C.) | Vacuum (mTorr) | Time (min.) | Comment |
|---|---|---|---|
| −50 | atm. | 120 | hold |
| −46 | 40 | 570 | hold |
| −36 | 40 | 500 | ramp |
| −36 | 40 | 150 | hold |
| 0 | 40 | 60 | ramp |
| 0 | 40 | 90 | hold |
| 28 | 40 | 14 | ramp |
| 28 | 40 | 270 | hold |

TABLE 4

| Temperature (°C.) | Vacuum (mTorr) | Time (min.) | Comment |
|---|---|---|---|
| −50 | 40 | 120 | hold |
| −46 | 40 | 600 | hold |
| −36 | 40 | 250 | ramp |
| −36 | 40 | 300 | hold |
| 0 | 40 | 400 | ramp |
| 0 | 40 | 300 | hold |
| 28 | 40 | 233 | ramp |
| 28 | 40 | 240 | hold |

Other protocols work as well, but the preferred protocol is the Table 4 method. Spheres made by the described method have a moisture content of less than 10% but preferably 2%–6%. The spheres had a diameter of 0.07 to 0.11 inches. The mass of the spheres was 1 to 3 mg.

Thus, a suitable drying program produces a reagent sphere having an acceptable hardness, size, shape, $T_g$, porosity, solubility, and stability (as determined by a functionality test like that in Example 1).

A sphere of the present invention is room temperature stable. By "room temperature stable," we mean that the sphere can be stored at 22° C. for greater than 6 months with less than 20% loss of enzymatic activity as compared to the activity measured after the reagents are first dried. One could also do accelerated stability studies at higher temperatures. By this method, one could predict 6 months of room temperature stability by incubating the sphere at temperatures up to 55° C. for 6 weeks (*Stability Testing in the EC, Japan, and the USA Scientific and Regulatory Requirements.*, Eds., W. Grimm and K. Krummer, pp. 75–94 (1993), Wissenschaftliche Verlagsgesellschaft mbH, Stuttgart).

A reagent sphere of the present invention has a $T_g$ of at least 10° C. A typical $T_g$ of the reagent spheres was 40° C. A $T_g$ of at least 40° will guarantee stability at room temperature (22° C.). A preferred $T_g$ is 45° C. $T_g$ is the glass transition temperature. It is the temperature above which the viscosity of a glassy material drops rapidly and the glassy material turns into a rubber, then into a deformable plastic which at even higher temperatures turns into a fluid.

The glass transition temperature ($T_g$) is used as an important indicator of stability of the spheres. At temperatures below or near the $T_g$ the sample remains as a stable glass. As the temperature rises above the $T_g$, the sample becomes a rubber and is less stable. The $T_g$ is measured using differential scanning calorimetry. 2–5 mg (1–2 spheres crushed) of sample are put into an aluminum pan. The $T_g$ of the sample is determined by subjecting the sample to a controlled temperature program from 0° C. to 100° C. at a rate of 10° C./min. The heat flow to and from the sample is measured and expressed as a shift in the baseline. The $T_g$ is expressed as the temperature at the midpoint of this baseline shift.

A typical porosity will allow dissolution of the sphere in 20 µl of water in 1 minute or less. A preferred porosity will allow dissolution in 30 seconds or less.

EXAMPLES

Example 1

Preparation of Restriction Enzyme Spheres

Several restriction enzymes have been stabilized by the process of the present invention, including EcoRI, BamHI, HindIII, PstI, and HaeIII. Each 10 ul sphere contained:

| | |
|---|---|
| 28 mM | Tris pH 7.5 |
| 160 mM | KCl |
| 2.8 mM | DTT |
| 0.08 mM | EDTA |
| 100 mM | NaCl |
| 20 mM | $MgCl_2$ |
| 0.08% | Tx-100 |
| 200 ug/ml | BSA |
| 20 units | Restriction Enzyme |
| 12.5% | Ficoll400 |
| 5% | Melezitose |

Dispensing and drying were performed as described above. The drying protocol was identical to that disclosed in Table 3 above. A Perkin Elmer DSC7 showed a glass transition temperature ($T_g$) of 66° C. to 71° C. for the spheres. The Karl Fisher Analysis yielded a moisture of 2.6% to 4.2%. The spheres dissolved in less than 30 seconds when 20 ul of water was added.

1 ug of lambda DNA was incubated with the stabilized enzyme buffer mixture at 37° C. for 1 hour. After digestion, the DNA was examined on an agarose electrophoretic gel. The banding pattern on the agarose gel showed the same banding pattern as a control sample.

The spheres were stable after 4 months storage at both room temperature and 37° C.

After 4 months storage at both room temperature and 37° C. the enzymes were tested again and found to have retained 100% of activity compared to the sample tested immediately after drying.

Example 2

Preparation of DNA Labelling Spheres

Mixtures containing enzymes and other reactants necessary for labelling DNA molecules were stabilized as spheres. Each 10 ul sphere contained:

| | |
|---|---|
| 50 mM | Tris pH7.5 |
| 50 mM | MgCl$_2$ |
| 50 mM | DTT |
| 250 mM | NaCl |
| 4 u/ml | d(N)$_9$ |
| 2.5 mg/ml | BSA |
| 20 units | FPLCpure Klenow (cloned Klenow fragment from DNA polymerase, Pharmacia Biotech) |
| 500 uM | dNTP's |
| 7.5% | Ficoll400 |
| 7.5% | Ficoll70 |
| 10% | Melezitose |

The spheres were dispensed and dried as described above. The drying protocol was that described in Table 4 above. A Perkin Elmer DSC7 showed a T$_g$ of 77° C. The Karl Fisher analysis yielded a moisture of 2%. The sphere dissolved in less than 30 seconds upon addition of 50 ul of water.

The functionality of the enzymes and reagents was tested by resuspending a sphere to a final volume of 50 ul with water and 25 ng lambda HindIII fragments and 50uCi$^{32}$αP-dCTP. After incubating at 37° C. for 15 minutes there was 45% to 50% incorporation of label. The probes had a specific activity of at least 1×10$^9$ cpm/ug.

Example 3

Preparation of First Strand Synthesis Spheres

A mixture with enzymes and reactants necessary for the synthesis of the first strand in a cDNA synthesis reaction were prepared in the method of the present invention. The formulation was as follows:

| | | |
|---|---|---|
| 41.25 mM | Tris pH 8.3 | |
| 8.25 mM | MgCl$_2$ | |
| 61.9 mM | KCl | |
| 6.2 mM | DTT | |
| 0.62 mg/ml | BSA | |
| 1.15 mM | dNTP's | |
| 15 units | RNAGARD | (Ribonuclease Inhibitor, Pharmacia Biotech) |
| 60 units | MMLV-RT | (cloned Molony Murine Leukemia Virus Reverse Transcriptase, Pharmacia Biotech) |
| 7.5% | Ficoll400 | |
| 7.5% | Ficoll70 | |
| 5% | Melezitose | |

The dispensing and drying protocol was identical to that described above. The spheres were dried according to the Table 4 procedure described above.

Each cDNA reaction required 2 spheres that were resuspended in 33 ul. The spheres dissolved in less than 30 seconds upon contact with water. The spheres had a T$_g$ of 54° C. The moisture content was 2%.

5 ug/ml of the Not-dT primer and 25 ng of rabbit globin mRNA were added to each reaction and incubated at 37° C. for 30 minutes. After performing a second strand synthesis reaction, the expected 7.5 Kb band was present on the gel.

Example 4

Preparation of PCR Spheres

Enzymes and reactants necessary for PCR reactions were prepared as spheres. The formulation of the 10 ul spheres was as follows.

| | |
|---|---|
| 100 mM | Tris pH 8.3 |
| 500 mM | KCl |
| 15 mM | MgCl$_2$ |
| 1 mg/ml | BSA |
| 2 mM | dNTP's |
| 8 units | AmpliTaq DNA Polymerase (Perkin Elmer) |
| 7.5% | Ficoll400 |
| 7.5% | Ficoll70 |
| 10% | Melezitose |

The dispensing and drying procedures were described above. The drying protocol was identical to that described in FIG. 4 above. Each sphere was resuspended in 100 ul of water. The sphere dissolved in less than 30 seconds. The T$_g$ is 68.3° C. 25 pmoles of RAPD-2 primer (Pharmacia Biotech) and approximately 500 ng of mouse spleen DNA were added to each reaction. A product was generated, but the MgCl$_2$ and Taq polymerase concentration need to be optimized to give results comparable to an optimized liquid control.

Example 5

Preparation of Transcription Spheres

Enzymes and reactants necessary for DNA transcription reactions were prepared as spheres. The formulation of each 10 ul sphere was as follows.

| | |
|---|---|
| 100 mM | Tris pH 8.0 |
| 25 mM | MgCl$_2$ |
| 10 mM | Spermidine |
| 25 mM | DTT |
| 125 ug/ml | BSA |
| 25 mM | NaCl |
| 1.25 mM | ATP |
| 1.25 mM | CTP |
| 1.25 mM | GTP |
| 0.75 uM | UTP |
| 10 units | RNAgard |
| 20 units | T7 RNA Polymerase (Pharmacia Biotech) |
| 5% | Ficoll400 |
| 7.5% | Ficoll70 |
| 5% | Melezitose |

The dispensing and drying procedures were described above. The drying protocol was identical to that described in FIG. 4 above.

Each sphere was resuspended to a final volume of 25 ul with water, 1 ug template (pTR1GAPDH), and 50uCi $^{32}$P-UTP. The spheres dissolved in less than 30 seconds upon contact with water. The T$_g$ was 40.3° C. The reaction is incubated at 37° C. for 30 minutes. Fresh reactions yielded 68.5% incorporation of label and 56 ng of RNA. The stabilized spheres yielded 65.5% incorporation and 60 ng of RNA.

Example 6

Preparation of Ligation Spheres

Enzymes and reactants necessary for DNA ligation reactions were prepared. Each 10 ul sphere contained the following formulation.

| | |
|---|---|
| 132 mM | Tris pH7.6 |
| 13.2 mM | MgCl$_2$ |
| 0.2 mM | ATP |

-continued

| | |
|---|---|
| 0.2 mM | Spermidine |
| 20 mM | DTT |
| 200 ug/ml | BSA |
| 20 units | T4 DNA Ligase (Pharmacia Biotech) |
| 5% | Ficoll400 |
| 7.5% | Ficoll70 |
| 5% | Melezitose |

The dispensing and drying protocol described above was followed. The drying protocol was identical to that described in Table 3. Each reaction sphere is resuspended in 20 ul of water. The spheres dissolve in less than 30 seconds upon contact with water. The $T_g$ was 35.7° C. The moisture content was 4.8%. 100 ng of pUC18 and 150 ng of Kan$^r$ genblock were ligated using the stabilized beads. 5 ng of the ligated DNA was added to 100 ul of NM522 competent cells and transformed, resulting in 1.76×10$^6$CFU.

Example 7

Preparation of Sequencing Spheres

Enzymes and reagents necessary for sequencing DNA were stabilized as spheres. Each reaction required 5 spheres, 1 sphere containing the "enzyme premix" and 1 sphere for each of the termination reactions.

The enzyme premix sphere had the following formulation:

| | |
|---|---|
| 0.413 uM | each dNTP |
| 100 mM | NaCl |
| 5 units | T7 DNA Polymerase (Pharmacia Biotech) |
| 12.5% | Ficoll400 |
| 5% | Melezitose |

The termination reactions had the following formulation:

| | |
|---|---|
| 420 uM | dNTP's |
| 46.5 uM | dNTP |
| 7 uM | ddNTP |
| 20 mM | Tris pH 7.6 |
| 25 mM | NaCl |
| 5% | Melezitose |
| 12.5% | Ficoll400 |

The dispensing and drying protocol described above was followed. The drying protocol was identical to that described in Table 3. The enzyme premix sphere $T_g$ was 39.7° C. The moisture content of the spheres was 1.7 to 3.5%.

Example 8

Preparation of DNA Extraction Buffer Spheres

Extraction buffer used to purify plasmid DNA minipreps was stabilized by the present invention. 15 ul spheres were made, each containing:

| | | |
|---|---|---|
| 40 mg/ml | sephaglass | (glass fiber purchased from Schuller International and ground to specification 0.5μ ± 0.5μ) |
| 7M | Guanidinium HCl | |
| 50 mM | Tris pH 7.5 | |
| 10 mm | EDTA | |
| 2.5% | Ficoll400 | |
| 2.5% | Ficoll70 | |

The dispensing and drying procedures were described above. The drying protocol was identical to that described in FIG. 4 above. The high level of guanidinium may be masking the $T_g$ but there appears to be a transition at 35° C. pUC18 plasmid was purified using the spheres. Gel results showed comparable yield and purity compared to standard protocols.

Example 9

Anti-E Tag/HRP Antibody Spheres

Anti-E Tag/HRP antibody was stabilized by the method of the present invention. The Anti-E Tag antibody (Anti-E/HRP) is a secondary antibody conjugated to horseradish peroxidase used to detect bound E Tagged ScFv recombinant antibody. The Anti-E Tag antibody is used to detect the peptide tag ("E" Tag) located at the carboxyl terminus of single-chain fragment variable (ScFv) recombinant antibodies expressed using the pCANTAB 5E vector.

Each sphere contained anti-E/HRP plus 7.5% Ficoll400, 7.5% Ficoll70, and 10% melezitose. The drying protocol of Table 4 was followed. The $T_g$ was 74.9° C. The spheres were used in ELISA for detection of soluble E-Tagged antibodies. Sensitivity of detection was comparable between the spheres and fresh Anti-E/HRP conjugate.

We claim:

1. A reagent sphere comprising:
   at least one biological reagent; and
   a glass-forming filler material in a concentration sufficient to facilitate formation of a glassy, porous composition wherein the glass-forming filler comprises a mixture of a high molecular weight synthetic carbohydrate polymer and a second carbohydrate;
   wherein the reagent sphere is water soluble and has a $T_g$ of at least 10° C.

2. The sphere of claim 1 wherein the synthetic polymer has a molecular weight of at least 10,000.

3. The sphere of claim 1 wherein the synthetic polymer has a molecular weight of at least 50,000.

4. The reagent sphere of claim 1, wherein the sphere is capable of completely dissolving in 20 μl of aqueous solution in 1 minute.

5. The reagent sphere of claim 4, wherein the sphere is capable of completely dissolving in 30 seconds.

6. The reagent sphere of claim 1 having a moisture content of less than 10%.

7. The reagent sphere of claim 1 wherein the biological reagent is stable at room temperature storage.

8. The reagent sphere of claim 1 comprising a plurality of reagents.

9. The reagent sphere of claim 1 additionally comprising a third carbohydrate.

10. The reagent sphere of claim 1 wherein the reagent sphere has structural integrity.

11. The reagent sphere of claim 1 wherein the reagent is selected from the group consisting of RNA modifying enzymes, DNA modifying enzymes, restriction enzymes, nucleotides, and oligonucleotides.

12. The reagent sphere of claim 1 wherein the second carbohydrate is selected from the group consisting of melezitose, cellobiose, DEXTRANT10 resin, maltotriose, maltose, cyclodextran, sorbitol, trehalose, PEG, and sucrose.

13. The reagent sphere of claim 12 wherein the second carbohydrate is selected from the group consisting of melezitose cellobiose, DEXTRANT10 resin and maltotriose are chosen.

14. The reagent sphere of claim 1 wherein the second carbohydrate is melezitose.

15. The reagent sphere of claim 1 wherein the high molecular weight polymer is a synthetic carbohydrate polymer made by the copolymerization of sucrose and epichlorohydrin.

16. A reagent sphere comprising:
    at least one biological reagent, wherein the biological reagent is a chaotropic salt; and
    a glass-forming filler material in a concentration sufficient to facilitate formation of a glassy, porous composition wherein the glass-forming filler comprises a mixture of a high molecular weight synthetic carbohydrate polymer and a second carbohydrate;
    wherein the reagent sphere is water soluble and has a $T_g$ of at least 10° C.

17. A reagent sphere comprising:
    at least one biological reagent, wherein the biological reagent is capable of binding nucleic acids; and
    a glass-forming filler material in a concentration sufficient to facilitate formation of a glassy, porous composition wherein the glass-forming filler comprises a mixture of a high molecular weight synthetic carbohydrate polymer and a second carbohydrate;
    wherein the reagent sphere is water soluble and has a $T_g$ of at least 10° C.

18. A reagent sphere comprising:
    at least one biological reagent, wherein the biological reagent is an antibody; and
    a glass-forming filler material in a concentration sufficient to facilitate formation of a glassy, porous composition wherein the glass-forming filler comprises a mixture of a high molecular weight synthetic carbohydrate polymer and a second carbohydrate;
    wherein the reagent sphere is water soluble and has a $T_g$ of at least 10° C.

19. A reagent sphere comprising:
    at least one biological reagent, wherein the biological reagent is selected from the group consisting of DNA primers, DNA polymerases, and deoxyribonucleotides; and
    a glass-forming filler material in a concentration sufficient to facilitate formation of a glassy, porous composition wherein the glass-forming filler comprises a mixture of a high molecular weight synthetic carbohydrate polymer and a second carbohydrate;
    wherein the reagent sphere is water soluble and has a $T_g$ of at least 10° C.

20. A reagent kit comprising:
    at least one reagent sphere according to claim 1;
    a receptacle containing the reagent sphere; and
    a sealed foil pouch containing the tube and a desiccant.

21. The reagent kit of claim 20 further comprising a dispenser device adapted for individually dispensing the at least one reagent sphere.

22. A method of making a reagent sphere comprising the steps of:
    (a) providing an aqueous solution of a buffered biological reagent;
    (b) mixing a glass forming filler material with the buffered reagent solution to form a mixture wherein the concentration of the filler material is sufficient to facilitate formation of a glassy, porous composition having a spherical shape comprises a high molecular weight synthetic carbohydrate polymer and a second carbohydrate;
    (c) dispensing the mixture in the form of substantially uniform droplets;
    (d) collecting the droplets on an inert cryogenic medium to form spheres; and
    (e) drying the droplets, under conditions suitable for maintaining the spherical shape, to form the reagent sphere;
    wherein the reagent sphere is water soluble and has a $T_g$ sufficient for room temperature stability.

23. The method of claim 22 wherein the vacuum drying is continued so that the reagent sphere contains less than about 10% moisture.

24. The method of claim 22 wherein the reagent sphere has a diameter of about 2 mm to about 6 mm.

25. The method of claim 22 wherein the at least one reagent is unstable when alone in an aqueous solution at room temperature.

26. The method of claim 22 wherein the aqueous solution contains a plurality of reagents.

27. The method of claim 22 wherein the plurality of reagents react with each other when in aqueous solution.

28. The method of claim 22 wherein the reagent is selected from at least one of the group consisting of RNA, DNA, proteins, RNA modifying enzymes, DNA modifying enzymes, restriction enzymes, nucleotides, and oligonucleotides.

29. The method of claim 23 wherein the second carbohydrate is selected from at least one of the group consisting of melezitose, cellobiose, DEXTRANT10 resin, maltotriose, maltose, cyclodextran, sorbitol, trehalose, PEG, and sucrose.

30. The method of claim 29 wherein the second carbohydrate is selected from the group consisting of melezitose, cellobiose, DEXTRANT10 resin, and maltotriose.

31. The reagent sphere of claim 22 wherein the synthetic carbohydrate polymer is made by the copolymerization of sucrose and epichlorohydrin.

32. A reagent sphere made according to the method of claim 22.

* * * * *